United States Patent
Takahashi et al.

(10) Patent No.: US 6,677,983 B1
(45) Date of Patent: Jan. 13, 2004

(54) ELECTRONIC ENDOSCOPE

(75) Inventors: Tadashi Takahashi, Saitama (JP); Ryo Ozawa, Tokyo (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/467,151

(22) Filed: Dec. 20, 1999

(30) Foreign Application Priority Data

Dec. 24, 1998 (JP) .......................................... P10-368052

(51) Int. Cl.7 ................................................. H04N 7/18
(52) U.S. Cl. .......................................... 348/65; 348/72
(58) Field of Search .............................. 348/76, 74, 65, 348/72; 358/520; 382/128, 131; 600/101, 104, 117, 118

(56) References Cited

U.S. PATENT DOCUMENTS

| | | | |
|---|---|---|---|
| 4,868,645 A | * 9/1989 | Kobayashi | 358/98 |
| 4,885,634 A | * 12/1989 | Yabe | 358/98 |
| 4,967,269 A | * 10/1990 | Sasagawa et al. | 358/98 |
| 5,159,380 A | * 10/1992 | Furuya et al. | 354/415 |
| 5,830,121 A | * 11/1998 | Enomoto et al. | 600/117 |
| 6,080,104 A | * 6/2000 | Ozawa et al. | 600/180 |
| 6,120,435 A | * 9/2000 | Eino | 600/118 |

* cited by examiner

*Primary Examiner*—Vu Le
*Assistant Examiner*—Behrooz Senfi
(74) *Attorney, Agent, or Firm*—Greenblum & Bernstein, P.L.C.

(57) ABSTRACT

An electronic endoscope includes a processor by which an image captured by an endoscope is displayed on a screen of a monitor. Panel switches, a central processing unit (CPU), a magneto-optic disc and a RAM are mounted in the processor. A keyboard and the monitor are connected to the processor. By operating the panel switches, operation conditions of the devices, mounted in the processor or connected to the processor, are set. The set values, which are set by the panel switches or the keyboard, are temporarily stored in the RAM. The set values stored in the RAM are recorded in the magneto-optic disc at every regular time interval. When character information displayed on the screen of the monitor is renewed by operating the keyboard, the renewed character information is recorded in the magneto-optic disc.

11 Claims, 12 Drawing Sheets

WRITING POSITION

FIG. 10

MAGETO-OPTIC DISC

| P1 (Br) | v1 |
|---------|----|
| P2 (Bl) | v2 |
| P3 (Re) | v3 |
| P4 (En) | v4 |

(FILE)

← RAM

| m[0] | P1 |
|------|----|
| m[1] | P2 |
| m[2] | P4 |
| m[3] | P3 |

ELECTRONIC ENDOSCOPE

BACKGROUND OF THE INVENTION

1. Field of the Invention

The present invention relates to an electronic endoscope for inserting an endoscope into the stomach or other body cavity and displaying an image of the body cavity on a monitor for examination, and more particularly relates to a setting operation by which an operation condition of the electronic endoscope is set.

2. Description of the Related Art

Conventionally, there is known an electronic endoscope in which an operation condition, such as a brightness adjustment of an image, can be set. In such an electronic endoscope, when the a setting of the operation condition is carried out, the operation condition is changed in accordance with the setting, a set value entered by the setting is recorded in a memory. For example, when a brightness level of an image of the body cavity is set by handling a switch, the brightness of the image is changed based on the set value, and at the same time, a value of the brightness level is recorded in the memory. Then, when the endoscope is operated after the setting operation, by reading the set value from the memory, the electronic endoscope can be used in accordance with the set value.

However, when the setting of the operation condition is continuously performed, since the change of the operation condition and the recording operation of the set value to the memory are simultaneously carried out, the recording operation disturbs the change of the operation condition, and thus, the operation condition can not be instantly changed on change of the set value. For example, when the brightness level is substantially changed by continuous switching operations, a brightness adjustment of the screen might be delayed since the recording operation is continuously carried out. Thus, the change of the operation condition cannot be performed promptly on change of the set value.

On the other hand, regarding character information such as a name of a patient indicated by a monitor, in a conventional electronic endoscope, even when the character information is not changed, the character information might be recorded in the memory. Namely, the character information, which is rarely changed, is repeatedly recorded in the memory, and thus, a useless recording operation might be performed.

SUMMARY OF THE INVENTION

An object of the present invention is to provide an electronic endoscope in which a change of the operation condition is promptly performed when changing the set value, and further character information is recorded in a memory only when necessary.

According to the present invention, there is provided an electronic endoscope having a display processor, a setting processor and a set value recording processor.

The display processor radiates light, which is output from a light source, to an object through an endoscope, to obtain and display an image of the object on a screen. The setting processor determines set values by which an operation condition of at least one of the display processor and the electronic endoscope is adjusted. The set value recording processor temporarily stores the set values in a volatile memory, and reads the set values from the volatile memory to record the set values in a non-volatile memory at regular time interval.

BRIEF DESCRIPTION OF THE DRAWINGS

The present invention will be better understood from the description of the preferred embodiments of the invention set forth below, together with the accompanying drawings, in which:

FIG. 10 is a view showing an example of the switch variable recorded in a magneto-optic disc;

DESCRIPTION OF THE PREFERRED EMBODIMENTS

Figure 1:
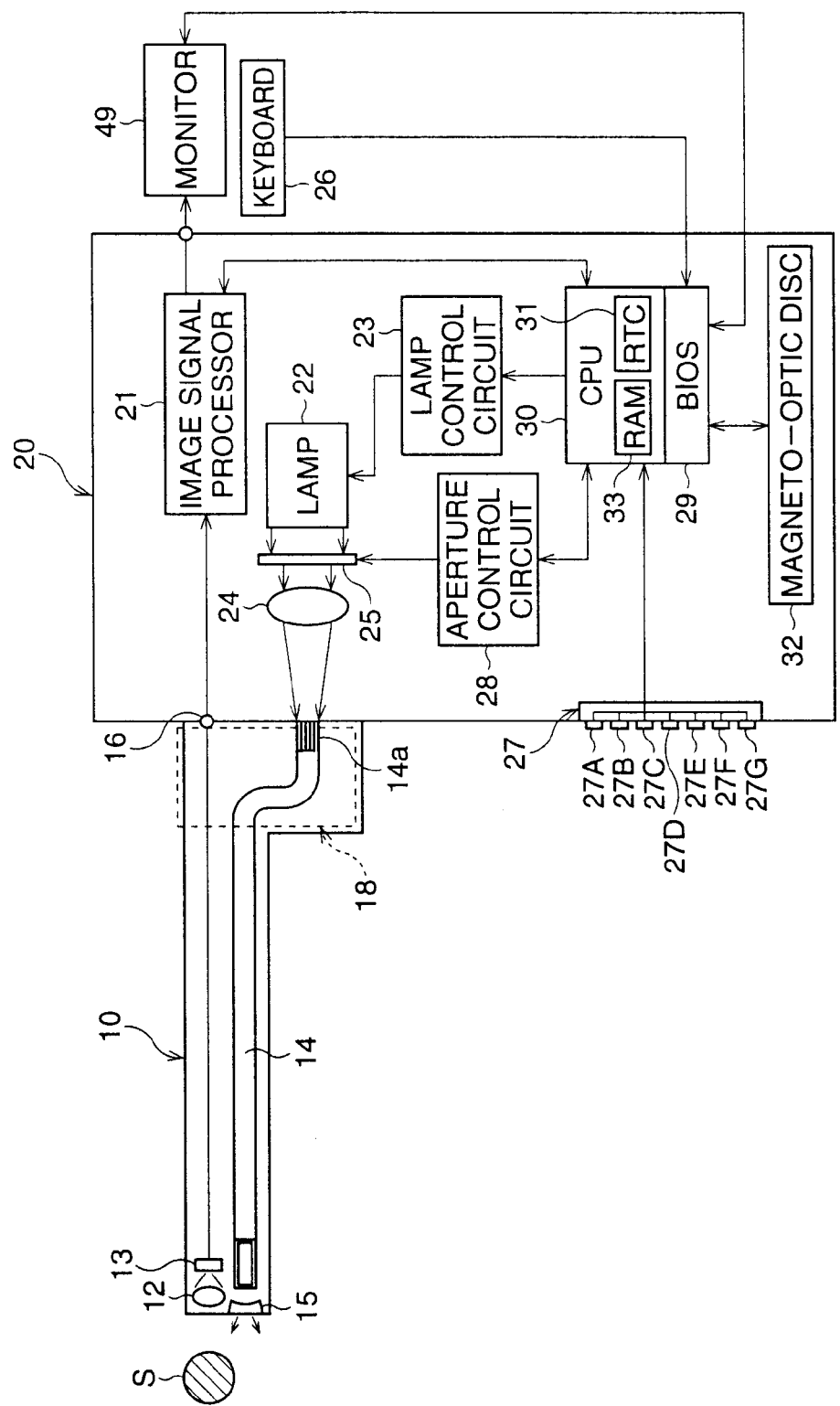
FIG. 1 is a block diagram of an electrical circuit of an electronic endoscope according to a first embodiment.

The present invention will be described below with reference to embodiments shown in the drawings.

FIG. 1 is a block diagram of an electrical circuit of an electronic endoscope according to a first embodiment.

An electronic endoscope has an video-scope 10 and a video-processor 20. A distal end of the video-scope 10 is inserted into the stomach or other body cavity S while a proximal end of the video-scope 10 is connected through a connection part 18 to the video-processor 20. A monitor 49 is connected to the video-processor 20 so that the image of the body cavity S is displayed on the monitor 49.

Inside the video-scope 10 is provided a light guide 14 through which light is passed from a lamp 22 serving as a light source. The light guided from the lamp 22 strikes an incidence end 14a of the light guide 14 due to a condenser lens 24 converging the light. The light passing through the light guide 14 passes through a diffusion lens 15 which expands the distribution angle of the light and irradiates the body cavity S. The amount of light irradiated in the body cavity S at that time is adjusted by an aperture 25 provided between the lamp 22 and a light collecting lens 24. The aperture 25 is opened and closed based on a signal sent from an aperture control circuit 28 so as to increase or decrease the amount of light.

The light irradiated in the body cavity S is reflected, so that the image of the body cavity S is formed on an imaging device 13 through the lens 12. On photo-diodes (not shown) arranged on a light receiving surface of the imaging device 13, red (R), green (G) and blue (B) color filter elements are disposed in a matrix arrangement, so that R, G and B image signals of the body cavity S are generated in the imaging device 13. The image signal corresponding to each of the colors is read from the imaging device 13 and transmitted through a connector 16 to the video-processor 20.

The image signal of the body cavity S, transmitted from the video-scope 10, is sent to an image signal processor 21. At the image signal processor 21, the image signal is separated into signals corresponding to the R, G, and B colors, each of which is subjected to a processing such as a gamma correction. Further, the R, G and B image signals are converted into a video signal including a luminance signal and color differential signals, and the luminance signal is transmitted to a central processing unit (CPU) 30 so that the aperture 25 is opened and closed to perform the light amount control.

The video signal output from the image signal processor 21 is added to a signal corresponding to character information, and is then transmitted to the monitor 49, where the image of the body cavity S and the character information regarding the body cavity S are indicated on the screen of the monitor 49. The character information includes data such as the name of the physician, the ID number of the patient and the current date and time.

The signal corresponding to the character information generated by operating a keyboard 26 is input to the CPU 30 through a basic input/output operating system (BIOS) 29, so that the character information is indicated by the monitor 49. Note that the BIOS 29 is a program group by which an input/output operation, between the CPU 30 and an external device such as the keyboard 26 and a magneto-optic disc 32 which are provided outside of the CPU 30, is controlled. The character information indicated by the monitor 49 is temporarily stored in a RAM (i.e., a volatile memory) 33, and is then recorded in the magneto-optic disc (i.e., a non-volatile memory) 32.

Panel switches 27 are provided with a switch for setting an operation condition such as a brightness adjustment, by which a brightness of an image displayed by the monitor 49, while the electronic endoscope is operated, is set. In the embodiment, four kinds of switches are provided in accordance with four operation conditions relating to a displayed image, such as a brightness adjustment of an image, a blue color adjustment, a red color adjustment of the image, and a contour enhancement of the image.

A brightness up switch 27A and a brightness down switch 27B are provided for adjusting a brightness level of the image displayed on the monitor 49. Namely, by operating the brightness up switch 27A, the brightness level is increased, and by operating the brightness down switch 27B, the brightness level is decreased. Similarly, by operating a blue color adjustment up switch 27C and a blue color adjustment down switch 27D, a blue component of the image displayed on the monitor 49 is adjusted, and by operating a red color adjustment up switch 27E and a red color adjustment down switch 27F, a red component of the image is adjusted.

A contour enhancement switch 27G is provided for enhancing a contour of an image of the body cavity S displayed on the monitor 49, by which obscureness of the image is corrected so that a clear image is obtained.

By operating the panel switches 27, signals relating to the operation condition are transmitted to the CPU 30. Then, set values relating to the operation condition are temporarily stored in the RAM 33. The set values stored in the RAM 33 are recorded in the magneto-optic disc 29 through the BIOS 29 at a regular time period.

A lamp control circuit 23 receives as input a signal for turning on a lamp 22. The lamp 22 is lit up by this input. In the CPU 30, the current date and time are read from a real time clock (RTC) 31, and are then displayed on the monitor 49.

Figure 2:
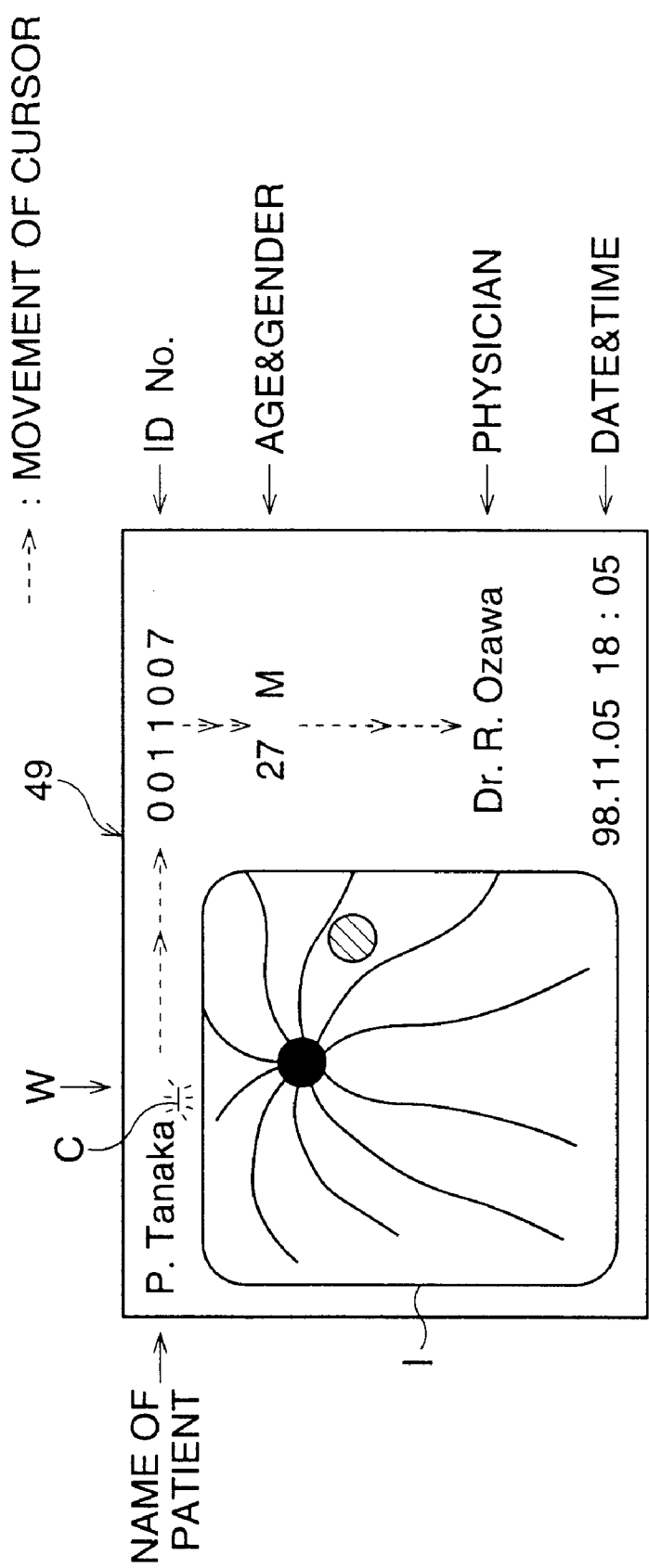
FIG. 2 is a view of a screen of a monitor.

FIG. 2 is a view of a screen displayed on the monitor 49.

On the screen W of the monitor 49, the image of the body cavity S is displayed in an image region I. Further, outside of the image region I, various items of character information are displayed. On a left-upper portion on the screen W, the name of the patient examined is indicated. On a right-upper portion on the screen W, the ID number of the patient, and his or her age and gender are indicated. On a right-lower portion on the screen W, the name of the physician conducting the examination, and the current date and time are indicated.

When a cursor C is indicated on the screen W, by operating a character key (not shown) on the keyboard 26, a character corresponding to the character key is indicated, and the cursor C is moved to a next right position. Then, when an enter key (i.e., an execution key, not shown) is operated after the completion of a renewal of character information of one item, the renewed character information is recorded in the magneto-optic disc 32, and the cursor C is moved to a top position of the next item of character information. For example, when the enter key is depressed after the name of the patient is input, the cursor C is moved to a top position of the ID number. When the cursor C is not indicated on the screen W, the cursor C is indicated at a top position of the name of the patient by depressing the enter key.

Figure 3:
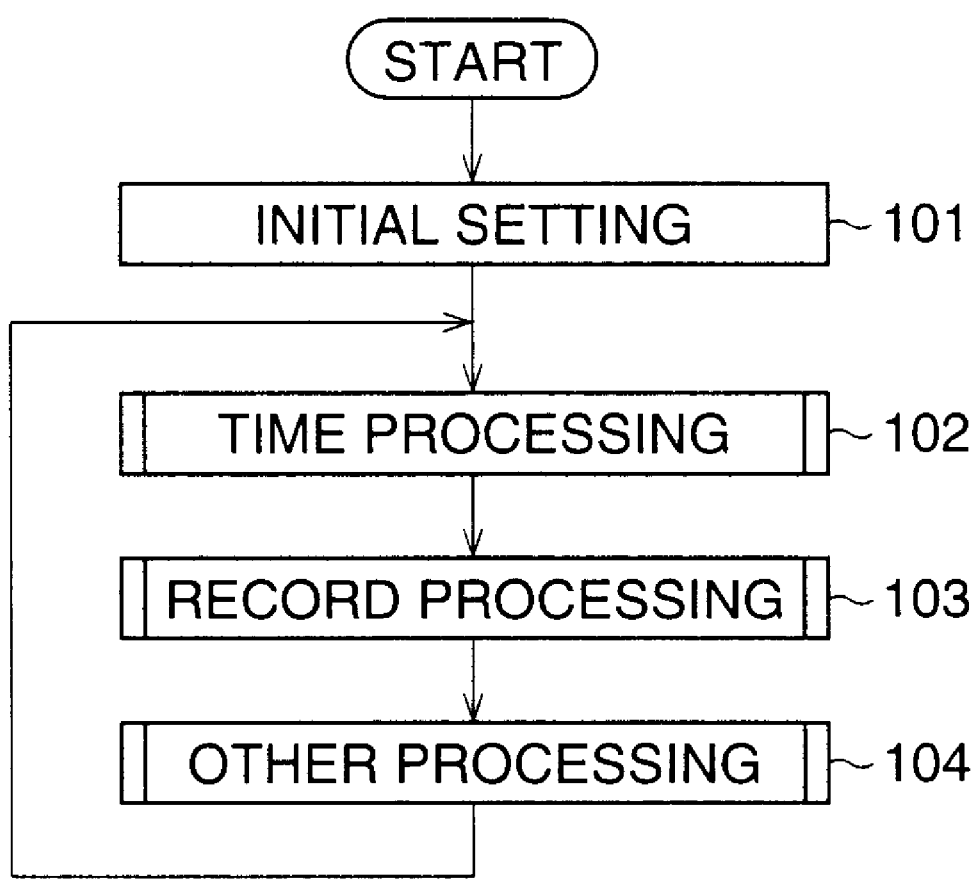
FIG. 3 is a flow chart of the operation of the electronic endoscope as a whole.

FIG. 3 is a flow chart showing the overall flow in the operation of the electronic endoscope as a whole. At step 101, by turning the power source on, the aperture 25 and various control use variables are set to their initial values.

At step 102, the current date and time are read from the RTC 31 of the CPU 30 (see FIG. 1), and the date and time are displayed on the monitor 49. At step 103, set values regarding the operation conditions set by a setting operation are recorded by the magneto-optic disc 32 at every regular interval when necessary.

At step 104, other processing is performed. For example, when the video-scope 10 is connected to the video-processor 20, the type name of the video-scope 10 is indicated on the screen W of the monitor 49.

The operation of the electronic endoscope is repeated until the power source is turned off. Subroutines are executed at step 102 to step 104. The subroutine executed at step 103 will be described later.

Figure 4:
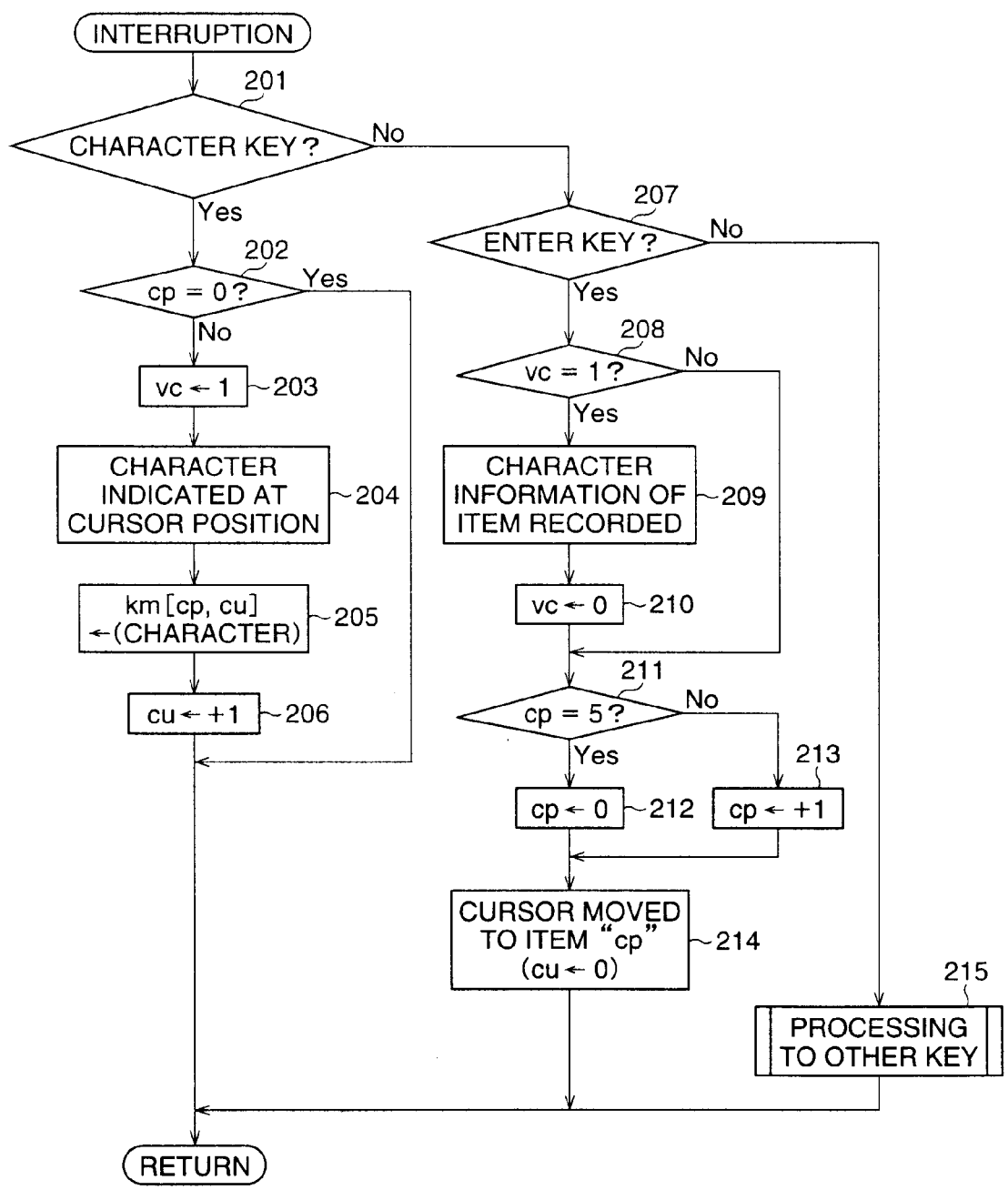
FIG. 4 is a flow chart of the interruption routine relating to the processing for the keyboard operation.

FIG. 4 is a flow chart of the interruption routine executed by operation of the keyboard 26 during the processing of step 102 to step 104 shown in FIG. 3.

At step 201, it is judged if a character key has been operated in the keyboard 26.

When it is judged that a character key has been operated, the routine proceeds to step 202, at which it is judged if the cursor C is indicated on the screen W. In the embodiment, the item of the character information, at which the cursor C is displayed, is indicated by a variable cp, as follows: an outside of the screen W (cp=0), the name of the patient (cp=1), the ID number (cp=2), the age (cp=3), the gender (cp=4), the name of the physician (cp=5). When it is judged that the cursor C is not displayed on the screen W (i.e., cp=0), step 203 through step 206 are skipped, and thus, this routine ends. Conversely, when it is judged that the cursor C is displayed on the screen W (i.e., cp≠0), the routine goes to step 203.

At step 203, a character variable vc, indicating if a character key has been operated, is set to "1". When a character key has not been operated, the character variable vc is "0". At step 204, a character, corresponding to the character key operated, is displayed at a position where the cursor C is indicated on the screen W.

At step 205, the character, input by the operation of the character key, is temporarily stored in a two dimensional array km[cp,cu] corresponding to addresses provided in the RAM 33 (shown in FIG. 1) in the CPU 30. Namely, the character input to the position cu of the cursor C in the item variable cp of the character information is stored in the array km[cp,cu]. For example, when the character "T" is input at a left end position (cu=0) of the name of the patient (cp=1), the character "T" is stored in the array km[1,0]. Then, at step 206, 1 is added to the cursor position cu, and the cursor C is moved to the next position on the right. When the input operation of one character is completed, this routine ends.

When it is judged that a character key has not been operated, the routine goes to step 207, at which it is judged if the enter key of the keyboard 26 has been operated.

When it is judged at step 207 that the enter key has been operated, the routine goes to step 208, at which it is judged if the character variable vc is equal to "1". Namely, it is judged if a character key had been operated before the enter key was operated so that new character information was input. When it is judged that the character variable vc is not equal to "1", i.e., when it is judged that a new character information was not input, step 209 through 210 are skipped, and thus the routine goes to step 211. When it is judged that the character variable vc is equal to "1", the routine goes to step 209.

Figure 5:
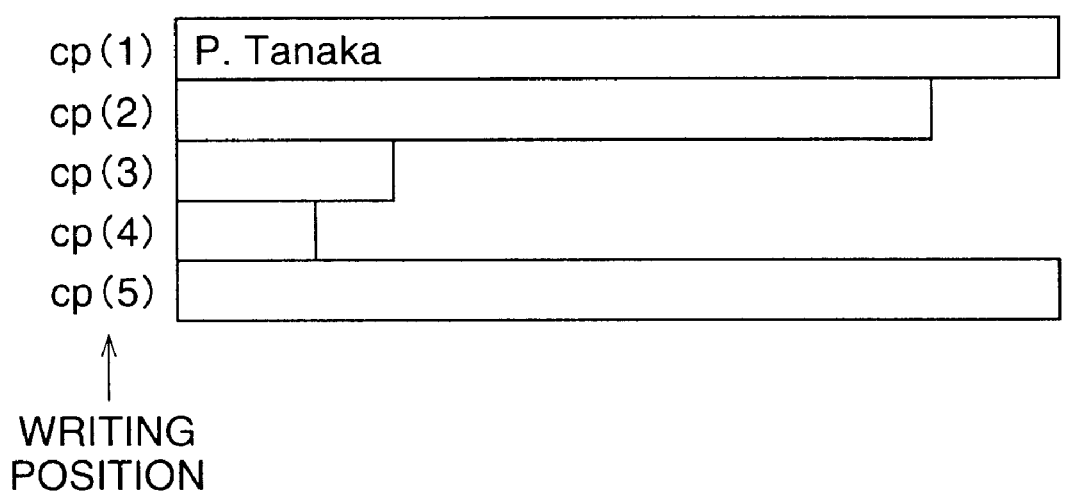
FIG. 5 is a view showing character information recorded in a magneto-optic disc.

At step 209, the character information of the item variable cp, at which the cursor C is displayed, is recorded in the magneto-optic disc 32 through the BIOS 29. At this time, the character information is written in a address corresponding to the item variable cp in a file provided in the magneto-optic disc 32, as shown in FIG. 5. Then, the character variable vc is set to "0" at step 210, and the routine then goes to step 211.

At step 211, it is determined if the item variable cp of the character information, at which the cursor C is indicated, is "5", i.e., if the item corresponds to the name of the physician. When it is judged that the item variable cp of the character information is "5", the routine goes to step 212, at which the item variable cp of the character information is set to correspond to an outside of the screen (cp=0), and the routine goes to step 214. Conversely, when it is determined at step 211 that the item variable cp of the character information is not "5", the routine goes to step 213, at which 1 is added to the item variable cp of the character information, so that a character can be input to the item variable cp of the character information. Then, the routine goes to step 214.

At step 214, the cursor C is moved to the item variable cp of the character information set at step 212 or step 213, and the position cu of the cursor C is set to "0" (i.e., the top position of the character information). Then, the interruption routine executed by the keyboard operation ends.

At step 207, when it is judged that the enter key has not been operated, the routine goes to step 215, at which processing relating to the other keys such as a function key is executed, and the routine ends.

Thus, only when character information of an item variable cp is renewed, the renewed character information of the item variable cp is recorded in the magneto-optic disc 32.

Figure 6:
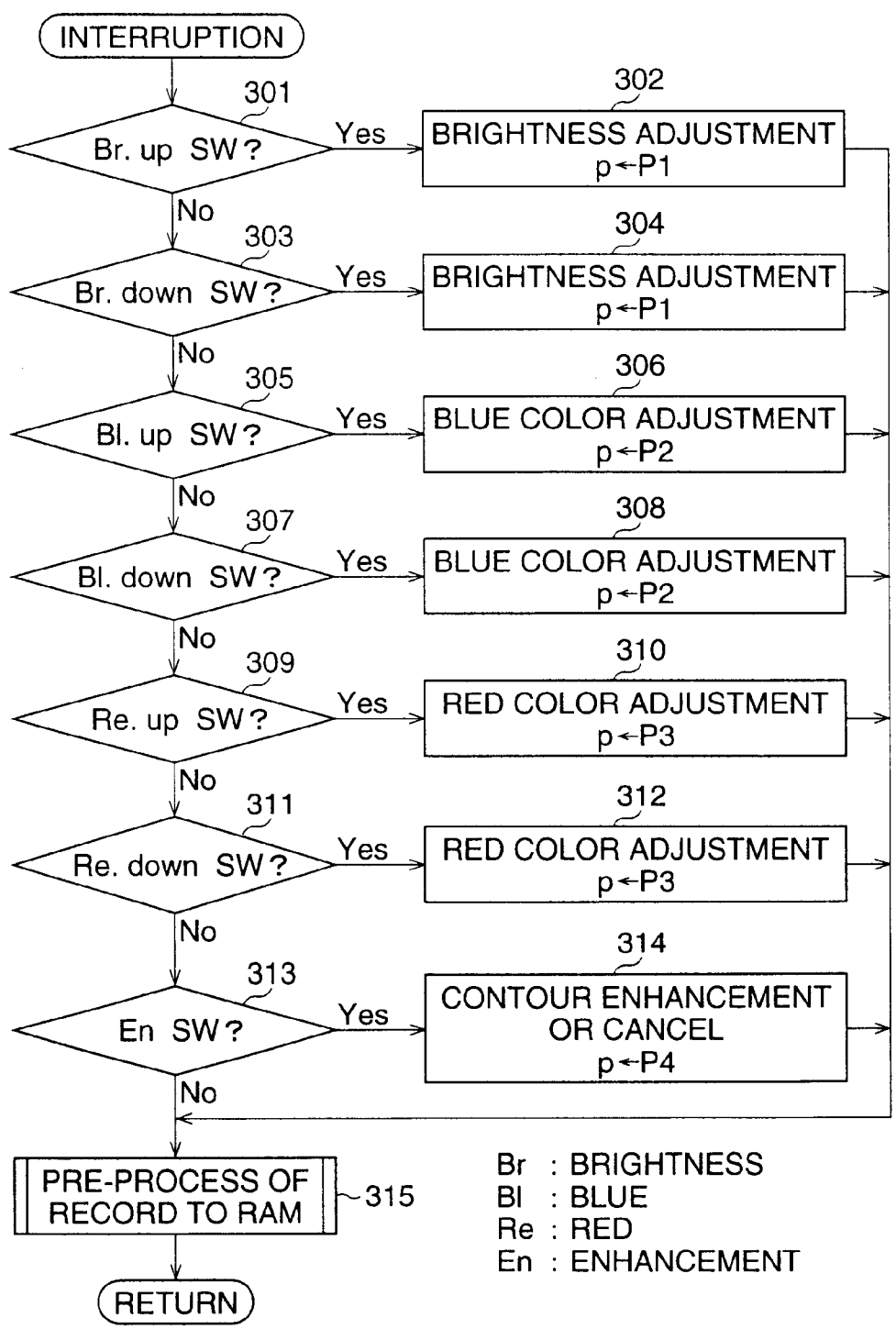
FIG. 6 is a flow chart of the interruption routine relating to the processing for the panel switch operation.

FIG. 6 is a flow chart of the interruption routine executed by operation of any one of the panel switches 27 during the processing of step 102 to step 104 shown in FIG. 3.

In this embodiment, it is assumed that a variable showing a value of a brightness level is "v1", a variable showing a value of a blue color level is "v2", a variable showing a value of a red color level is "v3", and a variable showing an ON/OFF state of a processing of a contour enhancement is "v4". The variable vn (n=1–3) is an integer between −3 and +3, and 0 is the standard value of the variable. The variable v4 is changed between "0"(i.e., OFF state) and "1" (i.e., ON state). By changing the values of the variables v1 through v4, the set values relating to the operation condition are changed.

At step 301, it is judged if the brightness up switch 27A has been operated. When it is judged that the brightness up switch 27A has been operated, the routine goes to step 302, at which the brightness level variable v1 is increased by "1", so that a brightness of an image on the monitor 49 is adjusted. Then, a writing position value P1 is substituted for a switch variable p, and the routine goes to step 315.

The writing position value Pn (n=1–4, wherein Pn≠0) indicates an address of the magneto-optic disc 32 on which the variables v1 through v4 (i.e., the set values) are recorded in a file in the magneto-optic disc 32, and corresponds to a number of the operation conditions which are to be set. Namely, the writing position value Pn corresponds to four operation conditions such as a brightness level adjustment, a blue color adjustment, a red color adjustment, and a contour enhancement of an image. The switch variable p is provided for substitution of the writing position values P1 through P4. Note that, when the panel switches 27 are operated, the set value set by the switching operation is stored in a predetermined address of the RAM, corresponding to one of variables v1 through v4.

When it is judged at step 301 that the brightness up switch 27A has not been operated, the routine goes to step 303, at which it is judged if the brightness down switch 27B has been operated. When it is judged that the brightness down switch 27B has been operated, the routine goes to step 304, at which the brightness level variable v1 is decreased by "1", so that a brightness of an image on the monitor 49 is adjusted. Then, the writing position value P1 is substituted for the switch variable p, and the routine goes to step 315. Conversely, when it is judged at step 303 that the brightness down switch 27B has not been operated, the routine goes to step 305.

At step 305, it is judged if the blue color adjustment up switch 27C has been operated. When it is judged that the blue color adjustment up switch 27C has been operated, the routine goes to step 306, at which the blue color level variable v2 is increased by "1", so that a blue color degree of an image on the monitor 49 is adjusted. Then, the writing position value P2 is substituted for the switch variable p, and the routine goes to step 315. Conversely, when it is judged at step 305 that the blue color adjustment up switch 27C has not been operated, the routine goes to step 307.

At step 307, it is judged if the blue color adjustment down switch 27D has been operated. When it is judged that the blue color adjustment down switch 27D has been operated, the routine goes to step 308, at which the blue color level variable v2 is decreased by "1", so that a blue color degree of an image on the monitor 49 is adjusted. Then, the writing position value P2 is substituted for the switch variable p, and the routine goes to step 315. Conversely, when it is judged at step 307 that the blue color adjustment down switch 27D has not been operated, the routine goes to step 309.

At step 309, it is judged if the red color adjustment up switch 27E has been operated. When it is judged that the red color adjustment up switch 27E has been operated, the routine goes to step 310, at which the red color level variable v3 is increased by "1", so that a red color degree of an image on the monitor 49 is adjusted. Then, the writing position value P3 is substituted for the switch variable p, and the routine goes to step 315. Conversely, when it is judged at step 309 that the red color adjustment up switch 27E has not been operated, the routine goes to step 311.

At step 311, it is judged if the red color adjustment down switch 27F has been operated. When it is judged that the red color adjustment down switch 27F has been operated, the routine goes to step 312, at which the red color level variable v3 is decreased by "1", so that a red color degree of an image on the monitor 49 is adjusted. Then, the writing position value P3 is substituted for the switch variable p, and the routine goes to step 315. Conversely, when it is judged at step 311 that the red color adjustment down switch 27F has not been operated, the routine goes to step 313.

At step 313, it is judged if the contour enhancement switch 27G has been operated. When it is judged that the contour enhancement switch 27G has been operated, the routine goes to step 314, at which a contour of an image of a body cavity S displayed on the monitor 49 is enhanced if the contour enhancement switch 27G is turned ON, and at which the contour enhancement of the image of the body cavity S is canceled if the contour enhancement switch 27G is turned OFF. Then, the writing position value P4 is substituted for the switch variable p, and the routine goes to step 315. Conversely, when it is judged at step 313 that the contour enhancement switch 27G has not been operated, the routine goes to step 315.

At step 315, a processing in which the switch variable p is stored in an array m[i] is executed. Then, the interruption routine relating to the panel switches 27 ends.

Figures 7, 8:
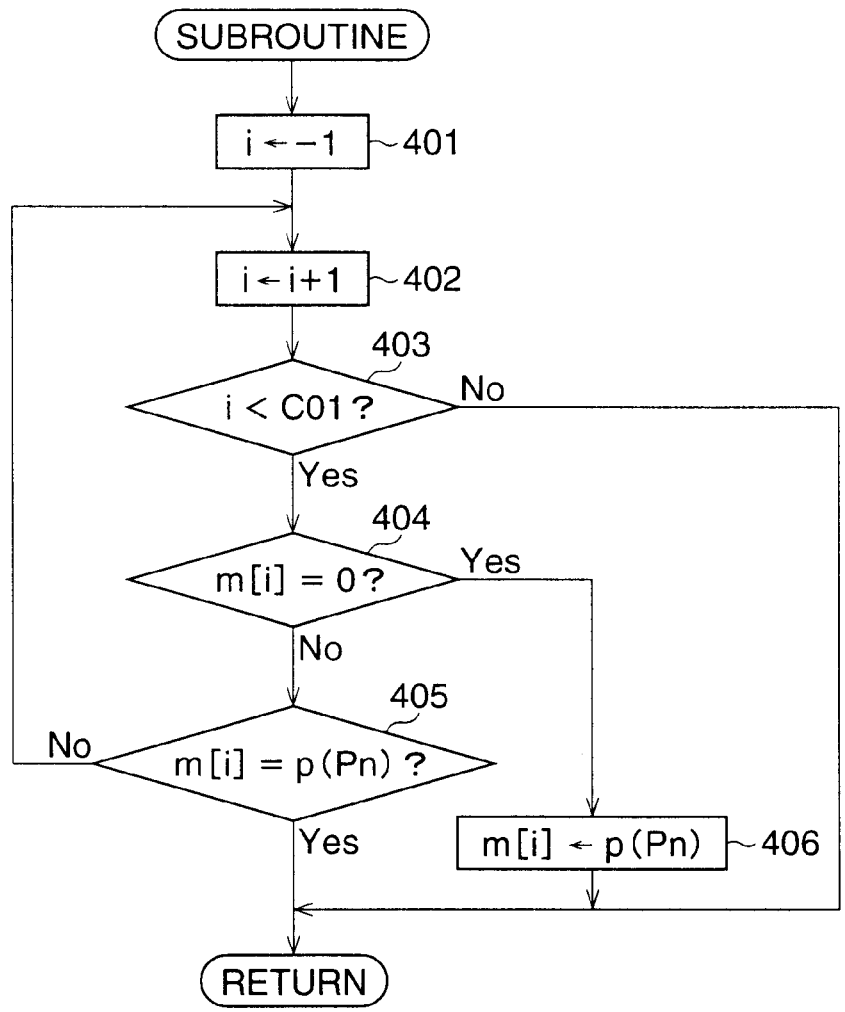
FIG. 7 is a flow chart of a subroutine executed in step 315 shown in FIG. 8.
FIG. 8 is a view showing an example of the switch variable.

FIG. 7 is a flow chart of the subroutine executed in step 315 shown in FIG. 6.

At step 401, "−1" is substituted for the variable i. Then, at step 402, "1" is added to the variable i. Note that the variable i indicates the element contained in the array m[i].

At step 403, it is judged if the variable i is less than a number of array elements C01. The panel switches 27 include four kinds of switches relating to brightness, blue color and red color adjustments, and a contour enhancement, and thus, the number of array elements C01 is 4. When it is judged that the variable i is less than the number of array elements C01, the routine goes to step 404, and when it is judged that the variable i is not less than the number of array elements C01, step 404 through step 406 are not executed, and thus the subroutine ends.

At step 404, it is judged if the array m[i] is "0". Namely, it is judged if the switch variable p has been stored in the array m[i] of the RAM 33. Note that the initial value of the array m[i](i=0–3) is "0".

When it is determined at step 404 that the switch variable p has not been stored in the array m[i], i.e., when it is determined that m[i] is "0", the routine goes to step 406, at which the switch variable p, which was substituted for by one of the writing position values P1 through P4 due to the executions of steps 301 through 314, is stored in the array m[i]. Then, the subroutine ends.

For example, when the brightness up switch 27A is first operated, the switch variable p for which the writing position switch P1 is substituted is stored in the array m[0].

When it is judged at step 404 that the switch variable p has been stored in the array m[i], the routine goes to step 405, at which it is judged if the switch variable p stored in the array m[i] is equal to the switch variable p set by the executions of step 301 through 314. Namely, it is judged if a switch, which was previously operated, has been again operated. When it is judged that the switch previously operated has been again operated, the subroutine ends. Conversely, when it is judged that the switch previously operated has not been again operated, the subroutine goes back to step 402.

For example, when the switch variable p (=P1) is stored first in the array m[0] at step 406 and the blue color adjustment up switch 27C is then operated, after step 402 through step 405 are executed, the routine goes back to step 402, so that step 402 through 404 and step 406 are executed, and thus, the switch variable p (=P2) is stored in the array m[1].

FIG. 8 shows an example of the switch variable p (=Pn) stored in the array m[i] in the RAM 33.

Figure 9:
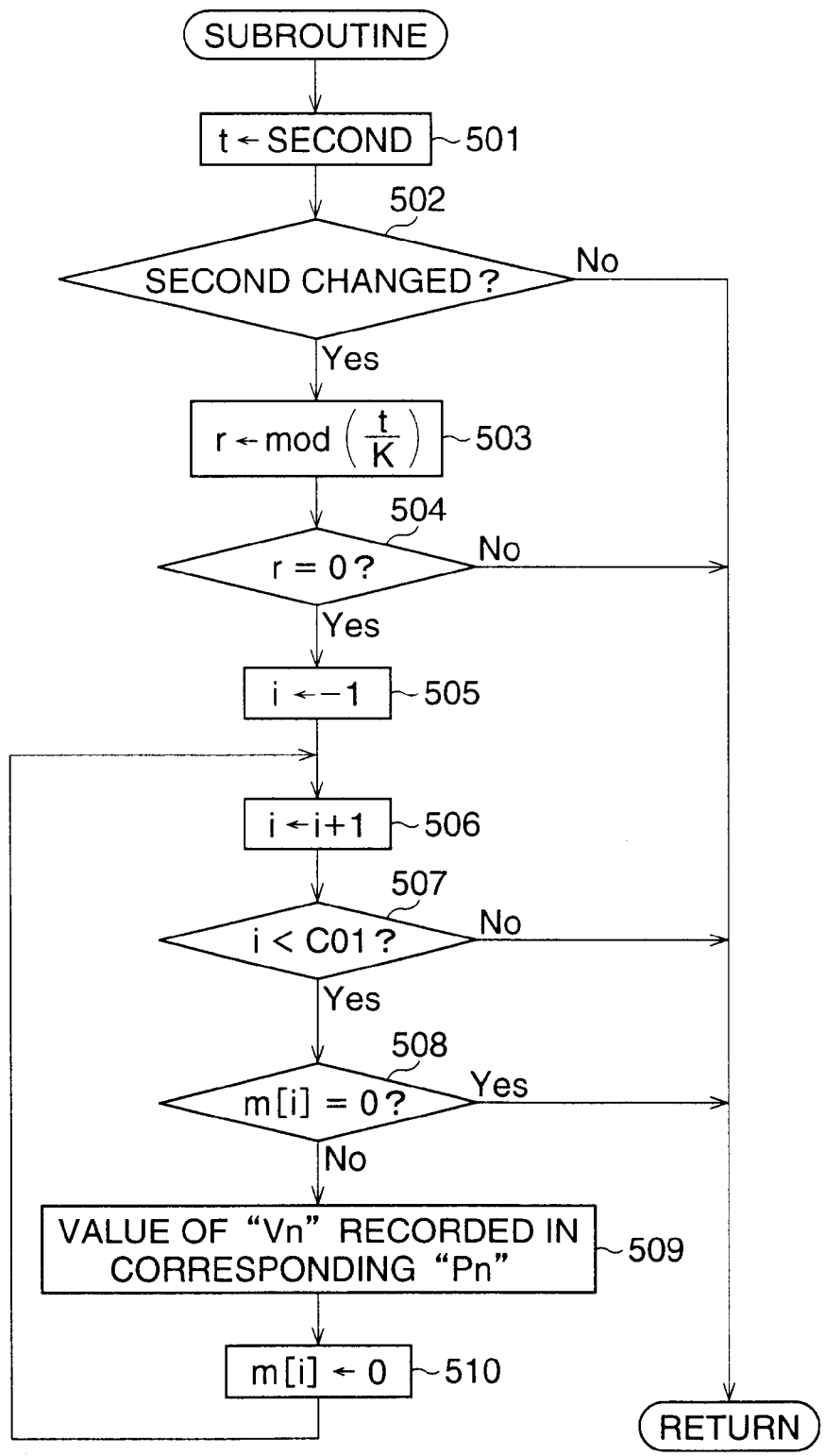
FIG. 9 is a flow chart of the subroutine executed in step 103 shown in FIG. 3, in the first embodiment.

FIG. 9 is a flow chart of the subroutine executed in step 103 shown in FIG. 3. With reference to FIG. 9, a recording processing by which the variables v1 through v4 are recorded in the magneto-optic disc 32 is described.

At step 501, a value of seconds of time, which is read from the RTC 31 (FIG. 1), is set for a second variable t. At step 502, the second variable t is compared with a second variable t0 which was obtained in the previous execution of the subroutine, so that it is judged if the value of seconds has changed. When it is judged that the value of seconds has changed, i.e., when it is judged that t0≠t, the second variable t is substituted for the second variable t0, the routine goes to step 503. Conversely, when it is judged that the value of seconds has not been changed (i.e., t=t0), step 503 through step 510 are not executed, and the subroutine ends.

At step 503, a remainder "r" is obtained by the following formula (1). Note that the interval constant K is 5, and "mod" means a calculation by which a remainder of the division is obtained.

$$r = \mathrm{mod}(t/K) \tag{1}$$

At step 504, it is judged if the remainder "r" obtained at step 503 is "0". Namely, it is judged if 5 seconds have passed since the execution of the previous recording processing. When it is judged that 5 seconds have passed, the routine goes to step 505. Conversely, when it is judged that 5 seconds have not passed, step 505 through step 510 are not executed, and the subroutine ends.

At step 505, "−1" is substituted for the variable i. Then, at step 506, "1" is added to the variable i.

At step 507, it is judged if the variable i is less than the number of array elements C01. When it is judged that the variable i is less than the number of array elements C01, the routine goes to step 508, and when it is judged that the variable i is not less than the number of array elements C01, step 508 through step 510 are not executed, and thus the subroutine ends.

At step 508, it is judged if the array m[i] is "0", i.e., if the switch variable "p" (=Pn) has been stored in the array m[i]. When it is judged that the switch variable p (=Pn) has been stored in the array m[i], the routine goes to step 509. Conversely, when it is judged that the switch variable p (=Pn) has not been stored in the array m[i], step 509 and step 510 are not executed, and the subroutine ends.

At step 509, the value of the variable vn (n=1–4) is recorded in the corresponding writing position variable Pn (n=1–4) of a file provided in the magneto-optic disc 32 (see FIG. 10). Then, at step 510, "0" is substituted for the array m[i]. Namely, the array m[i] is set to a state in which the switch variable p is not stored.

Step 506 through step 510 are repeatedly executed while the variable i is changed from "0" to "3", and when the changed set values, i.e., the variables v1 through v4 changed due to the switching operation are recorded in the magneto-optic disc 32, the recording processing to the magneto-optic disc ends.

Thus, in the first embodiment, the values of the variables v1 through v4 are recorded in the magneto-optic disc 32 concurrently at every 5 seconds, if the values have been changed.

As described above, according to the first embodiment, due to the executions of steps 501 through 510, only the changed variable vn, which relates to the operation condition set by operating the panel switches 27, is recorded in the magneto-optic disc 32 at every regular time interval. Thus, since the recording processing is performed only a necessary number of times when the variable vn corresponding to the set value is recorded in the magneto-optic disc 32, the recording processing is performed without disturbing the other processing. Note that, although the regular time interval is 5 seconds in the first embodiment, 30 seconds can be adopted as the regular time interval.

Further, in the first embodiment, even when the set value is continuously changed, the set value is recorded in the magneto-optic disc 32 at every regular time interval. Therefore, a useless recording processing to the magneto-optic disc 32 can be reduced.

A second embodiment is described below, which is the same as that of the first embodiment except in relation to the recording processing of the set value to the magneto-optic disc 32. Accordingly, an explanation of the second embodiment, except for the recording processing of the variables v1 through v4, is omitted.

Figure 11:
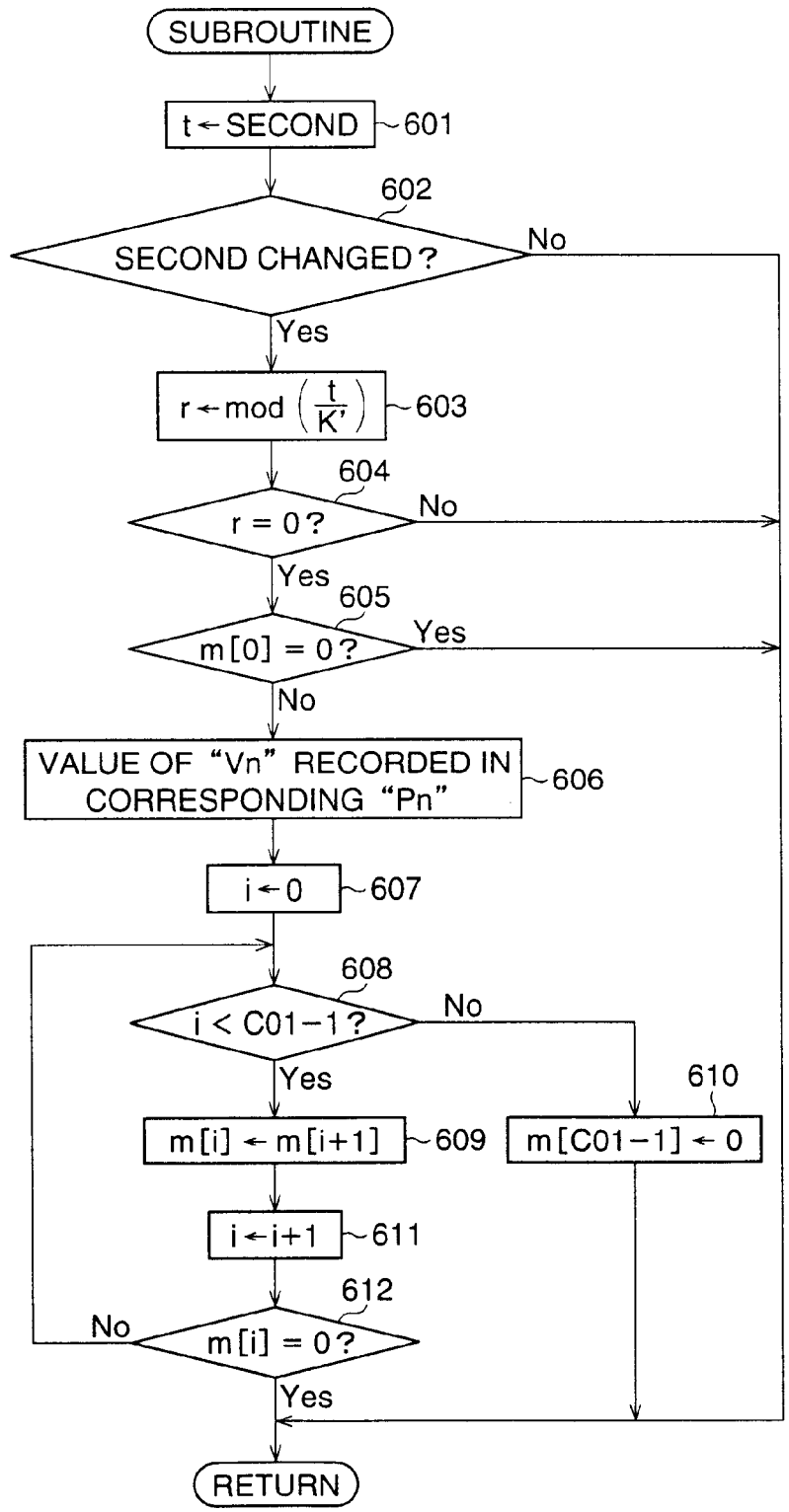
FIG. 11 is a flow chart of the subroutine executed in step 103 shown in FIG. 3, in a second embodiment.

FIG. 11 is a flow chart of the subroutine executed in step 103 shown in FIG. 3.

The contents of steps 601 and 602 are the same as those of steps 501 and 502 shown in FIG. 9 of the first embodiment.

At step 603, a remainder "r" is obtained according to the following formula (2). Note that the interval constant K' is 2.

$$r = \mathrm{mod}(t/K') \quad (2)$$

At step 604, it is judged if the remainder "r" is "0". Namely, it is judged if 2 seconds have passed since the execution of the previous recording processing. When it is judged that the remainder "r" is "0", the routine goes to step 605. Conversely, when it is judged that the remainder is not "0", step 605 through step 612 are not executed, and the subroutine ends.

At step 605, it is judged if the array m[0] is "0", i.e., if the switch variable p is stored in the array m[i]. When it is judged that the switch variable p is stored in the array m[0], i.e., that the array m[0] is not "0", the routine goes to step 606. Conversely, when it is judged that the switch variable p is not stored in the array m[0], i.e., that the array m[0] is "0", the subroutine ends.

At step 606, the value of the variable vn (n=1–4) is recorded in the corresponding writing position variable Pn (n=1–4) of a file provided in the magneto-optic disc 32.

At step 607, "1" is substituted for the variable i. At step 608, it is judged if the variable i satisfies the following formula (3) with respect to the number of array elements C01 (=4). Namely, it is judged if the variable i is less than "3".

$$i < C01 - 1 \quad (3)$$

Figure 12:
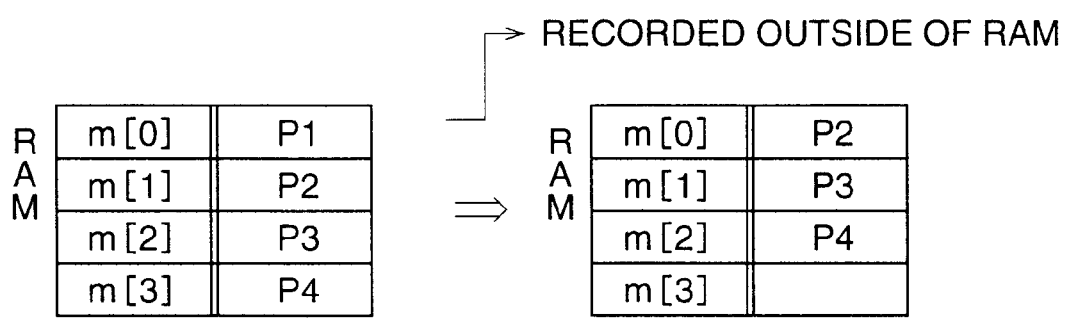
FIG. 12 is a view showing an example of the switch variable in the second embodiment.

When it is judged at step 608 that the variable i satisfies the formula (3), the routine goes to step 609, at which the switch variable p (=Pn), which has been stored in the array m[i+1], is moved to the array m[i] and stored there (see FIG. 12).

At step 611, "1" is added to the variable i. Then, at step 612, it is judged if the array m[i] is "0", i.e., if the switch variable p has been stored in the array m[i]. When it is judged that the array m[i] is "0", the recording processing to the magneto-optic disc ends. Conversely, when it is judged that the array m[i] is not "0", the routine goes back to step 608.

When it is judged at step 608 that the variable i does not satisfy the formula (3), i.e., when it is judged that the variable i is "3", the routine goes to step 610, at which "0" is substituted for the array m[C01-1]. Namely, the switch variable p is not substituted for the array m[C01-1]. Then, the subroutine ends.

Thus, in the second embodiment, only when it is judged in step 605 that the array m[0] is "0", steps 606 through 612 are executed, the variables v1–v4 are recorded in the magneto-optic disc 32 one by one at every 2 seconds, in accordance with an order in which the variables are stored in the RAM 33.

As described above, according to the second embodiment, since steps 606 through 612 are executed only when the array m[0] is "0", the processing is performed in a short time. Further, in a similar way as the first embodiment, due to the executions of steps 601 through 612, only the changed variables v1 through v4, which relate to the operation condition set by operating the panel switches 27, are recorded in the magneto-optic disc 32 at every regular time interval. Thus, when the variables v1 through v4 are recorded in the magneto-optic disc 32, the recording processing is performed without disturbing the other processing.

In the first and second embodiments, the panel switches 27 are provided with four kinds of switches by which an operation condition such as a brightness adjustment is set. However, in alternative embodiments, other various kinds of switches, for example, for the adjustment of image display conditions of the video-processor 20 and driving conditions of the video-scope 10, can be provided on the panel switches 27, as shown in FIG. 13.

Figure 13:
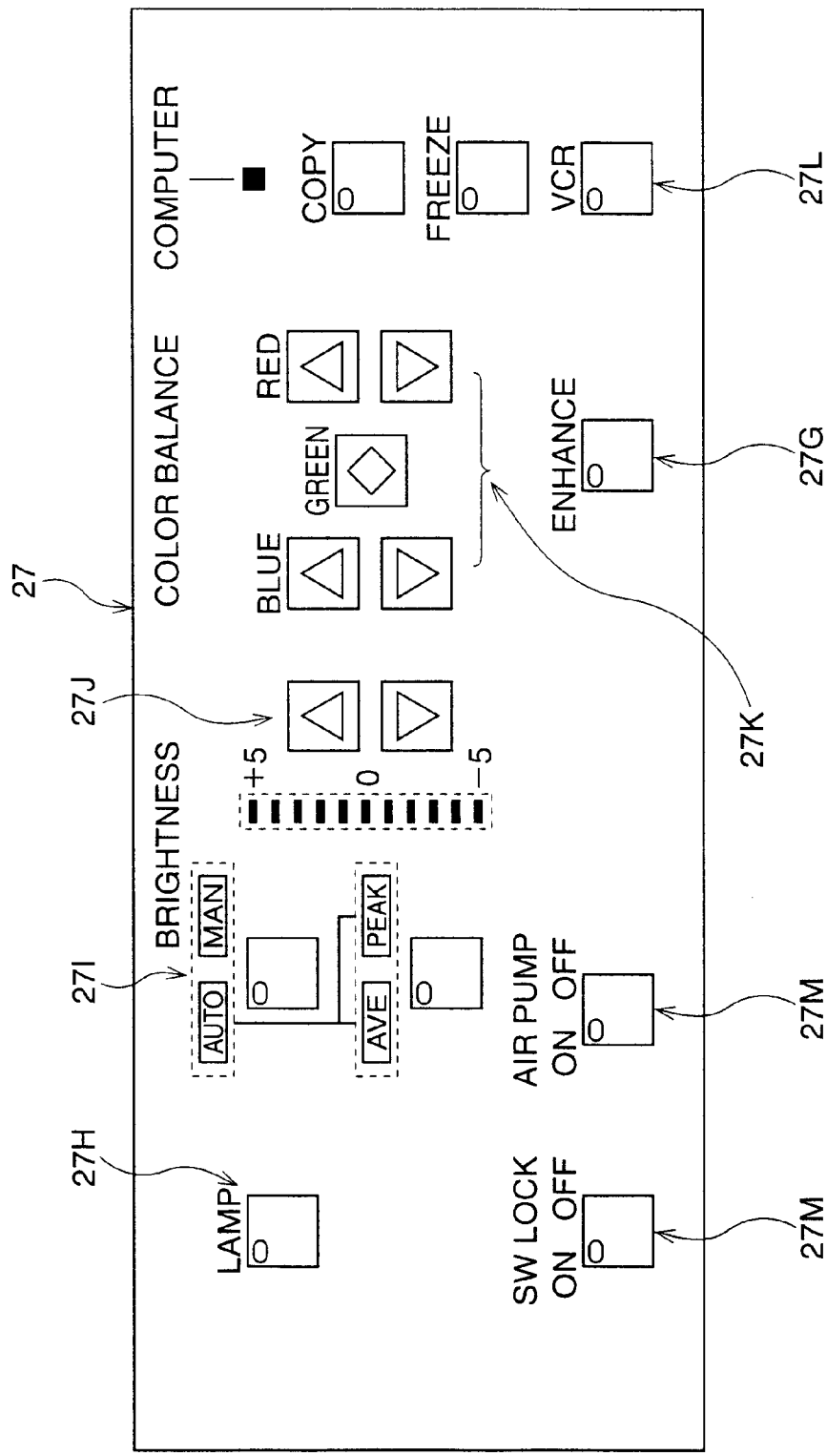
FIG. 13 is a view showing an example of the panel switch.

In FIG. 13, a lamp switch 27H is provided for turning ON and OFF the lamp 22. A brightness control selection switch 27I is provided for selecting a control method, by which a brightness of luminance light entering the light guide 14 is adjusted by a manual control and an automatic control. Brightness adjustment switches 27J are provided for manually adjusting a brightness of luminance light entering the light guide 14. Color balance switches 27K are provided for adjusting a color balance of an image displayed on the monitor 49.

External device control switches 27L are provided for making a hard copy of the image displayed on the monitor 49, freezing the image, and recording in a video tape. A pump switch 27M is provided for turning ON and OFF an air pump which supplies air to the body cavity S. A lock switch 27N is provided for locking conditions which are set by the lamp switch 27H, the color balance switches 27K and the pump switch 27M.

An ON-OFF condition of the lock switch 27N is changed by depressing the lock switch 27N. In the ON condition, even if the lamp switch 27H, the color balance switches 27K or the pump switch 27M is depressed, the depressing operation is ignored, and the set condition of the depressed switch is not changed. By depressing the lock switch 27N when the ON condition is set, the lock condition is released, so that operations of the lamp switch 27H, the color balance switches 27K and the pump switch 27M are re-activated.

Note that, although the magneto-optic disc 32 is adopted as the non-volatile memory in the first and second embodiments, in alternative embodiments, a hard disk and a flash memory can be used instead of the magneto-optic disk 32. Further, a time interval, at which the set value is recorded in the non-volatile memory, can be an arbitrary time from 2 seconds to 30 seconds.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 10-368052 (filed on Dec. 24, 1998) which is expressly incorporated herein, by reference, in its entirety.

What is claimed is:

1. An electronic endoscope comprising:
a display processor that radiates light output from a light source to an object, to obtain and display an image of said object on a screen;
a setting processor comprising an image display condition adjustment switch configured to set an image display condition by changing at least one of a plurality of variables each corresponding to a different image display condition of the image, said setting processor configured to determine set values set by said adjustment switch;
a set value recording processor that temporarily stores said set values in a volatile memory, and reads said set values from said volatile memory to record said set values in a non-volatile memory at a predetermined time interval, wherein said set value recording processor does not record set values corresponding to an unchanged variable of the plurality of variables in the non-volatile memory.

2. The electronic endoscope according to claim 1, further comprising a character information recording processor that temporarily stores character information of a predetermined item, which is indicated along with said image on said screen and is to be renewed, in said volatile memory, and reads said stored character information from said volatile memory to record said character information in said non-volatile memory.

3. The electronic endoscope according to claim 1, wherein said operation condition of said electronic endoscope includes a driving condition under which said electronic endoscope is driven.

4. The electronic endoscope according to claim 1, wherein said set value recording processor records said set values, stored in said volatile memory, in said non-volatile memory at said predetermined time interval, in accordance with an order in which said set values are stored in said volatile memory.

5. The electronic endoscope according to claim 4, wherein said set value recording processor records only a set value, which is renewed, in said non-volatile memory.

6. The electronic endoscope according to claim 1, wherein said predetermined time interval is between approximately 2 seconds and approximately 30 seconds.

7. The electronic endoscope according to claim 1, wherein said non-volatile memory is one of a magneto-optic disc, a flash memory and a hard disk.

8. The electronic endoscope according to claim 2, wherein said character information corresponds to said image displayed on said screen.

9. The electronic endoscope according to claim 2, wherein said character information recording processor does not record said character information in said non-volatile memory when said character information is not renewed.

10. The electronic endoscope according to claim 2, wherein said character information recording processor records said character information in accordance with an operation of an enter key after a character key is operated, said enter key and said character key being provided in a keyboard.

11. An electronic endoscope comprising:
a display processor configured to radiate light output from a light source to an object, said display processor further configured to obtain and display an image of the object on a screen;
a setter comprising an image display condition adjustment switch configured to set an image display condition by changing at least one of a plurality of variables each corresponding to a different image display condition of the image, said setting processor configured to determine set values set by said adjustment switch;
a set value recorder configured to store the set values in a first memory, said set value recorder further configured to read the set values from said first memory and record said set values in a second memory, wherein said set value recorder does not record set values corresponding to an unchanged variable of the plurality of variables in the second memory.

* * * * *